United States Patent [19]

Warnes et al.

[11] Patent Number: 4,704,479
[45] Date of Patent: Nov. 3, 1987

[54] PROCESS FOR PRODUCING METHYLOL KETONES

[75] Inventors: Paul R. Warnes, Flossmoor; James T. Henderson, Hindsdale; John P. Leja, Crestwood, all of Ill.

[73] Assignee: BTL Inc., Burlington, Canada

[21] Appl. No.: 428,582

[22] Filed: Sep. 30, 1982

Related U.S. Application Data

[63] Continuation of Ser. No. 144,974, Apr. 30, 1980, abandoned.

[51] Int. Cl.$^4$ .............................................. C07C 45/64
[52] U.S. Cl. .................................... 568/390; 568/313
[58] Field of Search ................................ 568/390, 313

[56] References Cited

U.S. PATENT DOCUMENTS

| 1,955,060 | 4/1934 | Flemming et al. | 568/390 |
| 2,303,370 | 12/1942 | Kugler et al. | 568/390 |
| 2,395,414 | 2/1946 | Lincoln et al. | 568/390 |
| 2,450,646 | 10/1948 | Dreisbach et al. | 568/390 |
| 2,711,971 | 6/1955 | Miller et al. | 568/390 |
| 4,326,086 | 4/1982 | Mohring et al. | 568/390 |

Primary Examiner—James H. Reamer
Attorney, Agent, or Firm—Edward D. Gilhooly

[57] ABSTRACT

Methylol ketones are produced by reacting a ketone with an aldehyde in the presence of a tertiary amine catalyst. The resulting polyols undergo the reactions common to beta hydroxy ketones, specifically, condensation reactions and substitution reactions involving the hydroxyl functionality; and addition reactions involving the carbonyl group. Each polyol molecule of the invention has from one to six hydroxyl groups in the beta position relative to the carbonyl group. The polyols are further characterized by complete water solubility and compatibility with a wide range of polymers, rendering these polyols useful as extenders and co-reactants.

10 Claims, No Drawings

PROCESS FOR PRODUCING METHYLOL KETONES

This is a continuation of application Ser. No. 144,974, filed Apr. 30, 1980, now abandoned.

FIELD AND BACKGROUND OF THE INVENTION

The present invention relates generally to new polyols and to an improvement in the process for making polyols. More particularly, the invention is directed to mono-, di-, tri-, tetra, penta and hexa-methylols produced by reacting ketones with formaldehyde and/or formaldehyde generators or donors.

The reaction between formaldehyde and acetone has been well characterized. As early as 1911, U.S. Pat. No. 989,993 (F. Bayer & Co.) described the condensation of acetone and formaldehyde in the presence of dilute alkali to form methylol acetone:

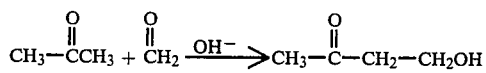

Later, Dreyfuss and Drewitt increased product yield and decreased by-product formation by using aqueous solvent systems and by maintaining the pH in a range between 8.5 and 9.5. (U.S. Pat. No. 2,387,933; British Celanese LTD). The product was once again monomethylol acetone.

The preparation of dimethylol acetone is described in U.S. Pat. No. 1,955,060 (I.G. Farbenindustrie A.G.). Dimethylol acetone can occur in unsymmetrical or symmetrical isomers:

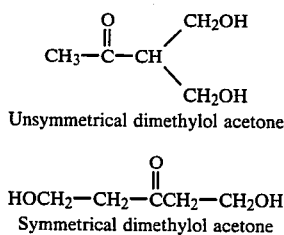
Unsymmetrical dimethylol acetone

HOCH$_2$—CH$_2$—CCH$_2$—CH$_2$OH
Symmetrical dimethylol acetone

Preparation of dimethylol acetone, in accordance with prior art techniques, involves reacting formaldehyde with acetone, using strong inorganic alkali catalysts to maintain the pH above 10.0.

The following mechanistic scheme is believed to describe the role of the strong alkali catalysts in the methylolation of acetone:

1. Abstraction of hydrogen atom from alpha carbon atom:

2. Reaction of carbanion with formaldehyde:

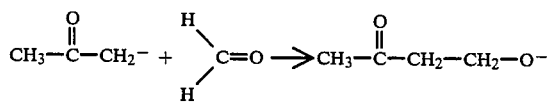

3. Regeneration of catalyst:

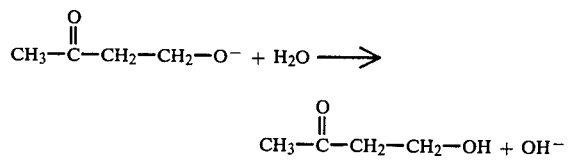

In theory, the above mechanism is repeatable to the extent of substituting up to three molecules of formaldehyde on each alpha carbon atom of acetone. However, the reaction conditions become more stringent as each additional hydrogen attached the the alpha carbon atom is replaced by a methylol group.

As indicated, the prior art technique has been to form methylol substituted acetone by and large from a reaction of the acetone carbanion with formaldehyde. Stronger alkali is required to form the carbanion as the alpha carbon atom becomes more highly substituted. Accordingly, only the mono-and di-methylol acetones are known in the prior art.

SUMMARY OF THE INVENTION

In accordance with the present invention, a surprising discovery has been made enabling one to provide tri-, and the tetra-methylol acetones or ketones in addition to the mono-, and di-methylol ketones.

As recognized in the prior art, the first hydrogen atom carried by the alpha carbon atom in ketones may be readily displaced or substituted. However, further substition becomes difficult, as indicated schematically below:

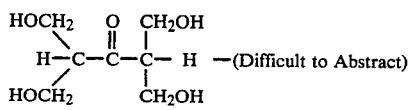
—(Difficult to Abstract)

Specifically, the remaining hydrogen atoms on the alpha carbon atoms are exceedingly difficult to abstract with alkali catalysts. In addition, as the alkali strength is increased, by-product formation becomes more a major consequence. Indeed, by-products such as diacetone alcohol, pinacol, methyl vinyl ether and various cyclic ethers are formed in greater amounts as alkali strength is increased.

A critical feature of the present invention is that it has been discovered that inhibited amines such as tertiary amine catalysts are effective to achieve a substitution of from one to six molecules of formaldehyde onto each molecule of ketone or acetone. In the system described, the reaction pH is kept moderately alkaline, that is, less than 10.0 so that by-product formation is held to a minimum.

While the mechanism of the reactions involved has not been conclusively established, it is believed that the tertiary amine catalyst complexes with the hydrogen atom attached the the alpha carbon atom of ketone or other acetone ketones. Thus up to six methylol groups substitute on each molecule of ketone. A product of this nature was previously thought impossible in the pH range achieved (below ten). In accordance with the method and the conditions of the process employed in the practice of the present invention, side reactions are minimized or eliminated completely. The following is an illustration of the mechanism believed to be involved in catalyzing formaldehyde substitution utilizing tertiary amine catalyst:

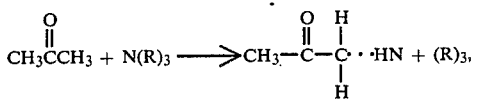

where R is other than a hydrogen atom, and where the three R radicals may be different.

A formaldehyde molecule is also partially polarized because of unshared pairs of electrons on its carbonyl oxygen:

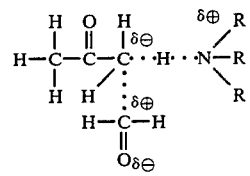

Thus, the tertiary amine helps polarize the acetone alpha carbon and helps coordinate the reactants for subsequent covalent bonding illustrated below are the structures of products formed in the practice of the present invention, in the reaction between acetone and formaldehyde with a trisubstituted amine as a catalyst:

| IUPAC Terminology | Structure | Common Terminology |
|---|---|---|
| 3-keto n-butanol (mw 88) | HO—CH$_2$—CH$_2$—C(=O)—CH$_3$ | mono methylol acetone |
| 3-keto,n-pentane 1,5-diol (mw 118) | HO—CH$_2$—CH$_2$—C(=O)—CH$_2$—CH$_2$—OH | sym. dimethylol acetone |
| 3-keto,2-(hydroxymethyl), butan-1-ol (mw 118) | (HO—CH$_2$)$_2$CH—C(=O)—CH$_3$ | unsym. dimethylol acetone |
| 3-keto,2-(hydroxymethyl), pentane 1,5-diol (mw 148) | HO—CH$_2$—CH$_2$—C(=O)—CH(CH$_2$—OH)$_2$ | trimethylol acetone |
| 3-keto,2,2$^1$ di(hydroxymethyl) butane 1-ol (mw 148) | CH$_3$—C(=O)—C(CH$_2$OH)$_3$ | trimethylol acetone |
| 3-keto,2,4 di(hydroxymethyl) pentane 1,5-diol (mw 178) | (HOCH$_2$)$_2$CH—C(=O)—CH(CH$_2$OH)$_2$ | tetramethylol acetone |
| 3-keto,2,2$^1$ di(hydroxymethyl) pentane 2,5-diol (mw 178) | HOCH$_2$—CH$_2$—CH$_2$—C(=O)—C(CH$_2$OH)$_2$—CH$_2$—OH | tetramethylol acetone |
| 3-keto,2,2' tri(hydroxymethyl) pentane 1,5 diol (mw 206) | (HOCH$_2$)$_2$CH—C(=O)—C(CH$_2$OH)$_3$ | penta methylol acetone |
| 3-keto,2,2',4,4'-tetrahydroxymethyl pentane 1,5 diol (mw 238) | (HOH$_2$C)$_3$C—C(=O)—C(CH$_2$OH)$_3$ | hexa methylol acetone |

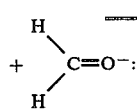

The various partial charges can then facilitate reaction between the partially positive formaldehyde carbon and the partially nagative alpha carbon on acetone, in accordance with the following mechanism:

DESCRIPTION OF THE PREFERRED EMBODIMENTS

Preferred embodiments of the invention are described below, by way of examples and not in any limiting sense. The following prodecure provided a tetramethylol substituted acetone.

EXAMPLE I

To a reaction vessel equipped for heating, cooling and agitation, there was added:

| Acetone | 7.5 mols |
|---|---|
| Formaldehyde | 30 mols |
| Triethylamine | 0.75 mol |

A solution as above, but containing only one-third of the triethyl amine was stirred well, heated to 50° C. and held at 50° C. for one hour. The remaining two-thirds of the triethylamine was then added and the mixture refluxed atmospherically for 45 minutes and cooled to room temperature. The resulting product had 53% solids content, a viscosity of 32 centipoises, a pH of 8.75, and exhibited infinite water dilutability. The final product, with 2% of unreacted formaldehyde, had a specific gravity of 1.1340.

The tri- and the penta-and hexa-methylol substituted products are obtained by using the appropriate substantially stoichiometric concentrational ratios of reactants.

The acetone used need not be anhydrous, and experiments have established the reaction mixture can indeed contain as much as 50% or more of water.

Formaldehyde in its various forms can be used effectively, including para-formaldehyde and standard preparations containing 65%, 55%, 45% or 37% of methanol-inhibited, formaldehyde solution or any other suitable formaldehyde donor.

The preferred basic catalyst employed in the reaction described, between the ketone and the aldehyde, is triethylamine. Other functionally equivalent (tri-substituted amines) compounds may be used.

In accordance with the invention, it has been found that the basic or alkaline nature of the organic catalyst is more efficient (than are inorganic alkaline agents) in driving the reaction to completion. The use of triethylamine, indeed, makes the reaction very exothermic and gives an efficiency of 95% yield or better based on formaldehyde consumed.

In contrast, it has been found that basic catalysts such as sodium hydroxide, barium hydroxide, calcium hydroxide, lithium hydroxide, as well as alkali metal and alkaline earth carbonates, or primary or secondary amines such as ammonia or diethylamine are not efficient catalysts or effective to drive the reaction to the desired end. Triethanol amine was also found not to drive the reaction to completion. It is, however, an important and unexpected discovery of the present invention that inhibited amine catalysts, that is, catalysts that are basic in nature and inhibited from reacting with the carbonyl group of the ketone, are exceedingly useful and effective in driving the ketone-aldehyde reaction to provide the end products desired.

The catalysts contemplated in the present invention are not limited to triethylamine alone, but include any tertiary amine having alkyl, aryl, or a combination of aryl-alkyl substituents, as well as tri-substituted amines, in general. Typical examples of tertiary amines include dimethyl aniline, trimethylamine, N, N-dimethyl toluidine and methyl diethylamine.

The reaction between acetone and formaldehyde, catalyzed by triethylamine in quantities sufficient ot maintain a minimum pH of 8.6, can be completed in 20 minutes to about four hours, depending upon the system temperature. The useful temperature ranges have been found to embrace the range of from about 40° C. to about 120° C. As the addition of the formaldehyde progresses, the boiling point of the reaction mass increases and, hence, the reaction temperature can be increased progressively, allowing the reaction to be completed more rapidly.

While the reaction has heen described with reference to acetone and formaldehyde as the reactants, those skilled in the art will appreciate that other ketones and other sources of the methylol group (—$CH_2$—OH) may be used, and that, in the light of the teachings of the present invention, such variations of the reaction taught may be conveniently carried out without any need to invoke the inventive faculty, and without any need for undue experimentation.

EXAMPLE II

The tetramethylol product of Example I was mixed with a phenol-formaldehyde resol on a 1 to 4 tetramethylol acetone to phenol-formaldehyde solids basis.

| phenol-formaldehyde (67% solids) | 2400 g |
|---|---|
| tetramethylol acetone (53% solids) | 800 g |

This mixture was then dehydrated to provide a system having the following characteristics.

| Viscosity | 330 cps | |
|---|---|---|
| Specific Gravity | 1.2072 | |
| Stroke cure | (150° C.) | 179 secs. |
| Sunshine gel | (135° C.) | 522 secs. |
| pH | 8.5 | |
| ASTM Solids | (135° C.) | 65% |

The utility of the resulting mixture was found to be two-fold. The tetramethylol acetone replaced the conventional and customary methanol solvent needed to solvate the phenolformaldehyde resol. Also, the tetramethylol acetone functions not only as a solvent for the phenolformaldehyde system, but also reacts with the system itself to become a component constituent thereof, rather than being flashed off as the methanol would be.

The use of tetramethylol acetone as a "solvent" as opposed to methanol may, depending upon the solubility of the polymerizing agent, yield a reaction system that is further dilutable with water. This novel aspect of the subject invention obviates the need to use the usual volatile organic diluents or solvents. The practical effect of the innovation is greatly to reduce fire hazards and effectively to eliminate atmospheric contamination.

The methyol and polymethylol ketones of the invention have been found to have a broad range of utilities:

1. As chemically reactive, co-polymerizable diluents for use with phenol-formaldehyde resins, melamine-formaldehyde resins, urea-formaldehyde resins, xyenol-formaldehyde resins, napthol-formaldehyde resins, aniline-formaldehyde resins, dicyandiamide-formaldehyde resins, furfuryl alcohol-formaldehyde resins, furfuraldehyde-phenol resins, cersol-formaldehyde resins, diphenol oxide-formaldehyde resins, bis-phenol-formaldehyde resins, benzoguanimine-formaldehyde resins, quinone-formaldehyde resins, hydro-quinone-formaldehyde resins, furan-formaldehyde resins, epoxy resins, nylon resins, poly ester resins, polyvinyl alcohol resins, resorcinol-formaldehyde resins, aromatic and aliphatic substituted phenol-formaldehyde resins, and silicones;

2. As co-reactants or curing agents for epoxy resins;

3. As chemically reactive polyols which are especially useful with isocyanate compounds to form urethane coatings, adhesives or foams, the low content of ionic species due to the tertiary amine catalyst insuring compatibility with isocyanate compounds;

4. As reactants with organic acids or acid anhydrides to form polyester resins useful as coatings, molding compounds, adhesives or foams;

5. As replacements for polyols such as pentaerythritol, trimethylol propane, ethylene glycol, diethylene glycol, propylene glycol, dipropylene glycol, polypropylene glycol or polyethylene glycol;

6. In alkyds, the acetone-formaldehyde resin is useful as a replacement for glycerine or related polyols for coatings and binders;

7. For compounding with phosphorous, sulfur, halogen or nitrogen containing substances for use as flame retardants.

Thus polyols of the invention may be co-polymerized or reacted with such cross linking material as isocyanates, blocked isocyanates, polymerized isocyanates, organic and inorganic acids, anhydride, amines and amides, and may be reacted with hydroxyl-containing materials such as alcohols, glycols, and polyols, and, generally, with polymerizable agents capable of reacting with an alcoholic hydrogen.

What is claimed is:

1. A process for producing polymethylol ketones, said process comprising:

reacting a ketone at a temperature of 40° C. to 120° C. selected from the group consisting of dialiphatic ketones, diaromatic ketones, aliphatic-aromatic substituted ketones, and mixtures thereof having from 3 to 6 hydrogen atoms attached to α carbon atoms atoms of said ketone with an aldehyde selected from the group consisting of formaldehyde and formaldehyde donor agents in an alkaline system having a pH of less than about 10 in the presence of a catalyst comprising an organic teriary amine under conditions free of solid phase catalysts to form polymethylol ketones having from 3 to 6 methylol groups attached to carbons of said ketones as substitutes for hydrogen atoms originally attached to said α carbon atoms.

2. The process as set forth in claim 1 wherein said tertiary amine is triethylamine.

3. The process as set forth in claim 1 wherein said ketone is acetone.

4. The process as set forth in claim 1 wherein said ketone is selected from the group consisting of dialiphatic ketones, diaromatic ketones, aliphatic-aromatic substituted ketones, and mixtures thereof.

5. The process of claim 1 in which said organic tertiary amine includes organic groups selected from the group consisting of alkyl, and combined alkyl-aryl groups having at least di alkyl amines.

6. A process for producing polymethylol ketones, said processing comprising:

reacting acetone with formaldehyde in the presence of an organic tertiary amine under alkaline conditions and free of solid phase catalysts, said organic tertiary amine includes organic groups selected from the group consisting of alkyl and combined alkyl-aryl groups having at least dialkylamines, said acetone is reacted at a temperature of 40° C. to 120° C., said alkaline conditions constitute a pH of less than 10.

7. The process of claim 1 wherein said organic tertiary amine is a dialiphatic or trialiphatic amine.

8. The process of claim 1 in which said organic tertiary amine is a dialkylamine or trialkylamine.

9. The process of claim 8 wherein said tertiary amine is a trialkylamine.

10. The process of claim 6 wherein said organic tertiary amine is a trialkylamine.

* * * * *